(12) United States Patent
Elmén

(10) Patent No.: US 9,808,580 B2
(45) Date of Patent: Nov. 7, 2017

(54) MEDICAMENT DELIVERY DEVICE

(71) Applicant: SHL Group AB, Nacka Strand (SE)

(72) Inventor: Gunnar Elmén, Huddinge (SE)

(73) Assignee: SHL Group AB, Nacka Strand (SE)

( * ) Notice: Subject to any disclaimer, the term of this patent is extended or adjusted under 35 U.S.C. 154(b) by 615 days.

(21) Appl. No.: 14/362,590

(22) PCT Filed: Nov. 28, 2012

(86) PCT No.: PCT/SE2012/051311
§ 371 (c)(1),
(2) Date: Jun. 3, 2014

(87) PCT Pub. No.: WO2013/085453
PCT Pub. Date: Jun. 13, 2013

(65) Prior Publication Data
US 2014/0331996 A1    Nov. 13, 2014

Related U.S. Application Data

(60) Provisional application No. 61/567,293, filed on Dec. 6, 2011.

(30) Foreign Application Priority Data

Dec. 6, 2011  (SE) .................................. 1151163-1

(51) Int. Cl.
*A61M 5/00* (2006.01)
*A61M 5/315* (2006.01)
(Continued)

(52) U.S. Cl.
CPC .......... *A61M 5/31536* (2013.01); *A61M 5/24* (2013.01); *A61M 5/3146* (2013.01);
(Continued)

(58) Field of Classification Search
CPC .......... A61M 5/31543; A61M 5/31553; A61M 5/31583; A61M 5/31581; A61M 5/31551;
(Continued)

(56) References Cited

FOREIGN PATENT DOCUMENTS

EP         1681070 A1    7/2006
WO    2009/101005 A1    8/2009
(Continued)

OTHER PUBLICATIONS

Sweden Patent Office, Int'l Search Report in PCT/SE2012/051311, dated Mar. 6, 2013.
(Continued)

*Primary Examiner* — Bradley Philips
(74) *Attorney, Agent, or Firm* — Piedmont Intellectual Property

(57) ABSTRACT

The invention relates to a medicament delivery device comprising a locking mechanism (5) for locking a plunger rod (4). The locking mechanism (5) comprises a locking wheel (6) and locking means (7), said locking means (7) being moveable between an active position where the locking means (7) prevent the locking wheel (6) from rotation and an inactive position where the locking means (7) allow the locking wheel (6) to rotate, wherein said plunger rod (4) extends through an opening in the locking wheel (6); and a resilient member (8) arranged at the moveable locking means (7) and being arranged to act on the moveable locking means (7) to displace said movable looking means (7) towards the inactive position where the locking means (7) allow the locking wheel (6) to rotate.

14 Claims, 7 Drawing Sheets

(51) Int. Cl.
    *A61M 5/24*     (2006.01)
    *A61M 5/31*     (2006.01)
    *A61M 15/00*     (2006.01)

(52) U.S. Cl.
    CPC .... *A61M 5/31543* (2013.01); *A61M 15/0001* (2014.02); *A61M 2005/2407* (2013.01)

(58) Field of Classification Search
    CPC ............ A61M 5/3155; A61M 15/0065; A61M 11/007; A61M 15/0001; A61M 2005/2407; A61M 5/24; A61M 5/3146; A61M 5/31536
    See application file for complete search history.

(56) References Cited

FOREIGN PATENT DOCUMENTS

| | | |
|---|---|---|
| WO | 2011/039203 A2 | 4/2011 |
| WO | 2011/089246 A1 | 7/2011 |

OTHER PUBLICATIONS

Sweden Patent Office, Written Opinion in PCT/SE2012/051311, dated Mar. 6, 2013.

MEDICAMENT DELIVERY DEVICE

FIELD OF THE INVENTION

The present invention relates to a medicament delivery device, especially a reusable injector or inhaler where the plunger rod is capable of adjustment with respect to a plunger of a medicament container during reloading with a new medicament container.

BACKGROUND OF THE INVENTION

Reusable delivery devices which can be reloaded with a new medicament container when a prior medicament container is emptied are known in the prior art. WO-2009/101005 describes an injector which is capable of an automatic adjustment of the plunger rod in relation to a plunger of a medicament cartridge. That injector comprises a dose setting mechanism capable of setting and resetting a dose of medicament and a drive nut connected to said dose setting mechanism. Said drive nut is rotatably coupled to the plunger rod by means of internal threads in an opening in the drive nut and external threads on the plunger rod. The injector further comprises a locking nut having an opening through which the plunger rod passes. The locking nut and the plunger rod are shaped such that an axial movement of the plunger rod relative to the locking nut is allowed while preventing a relative rotational movement between the plunger rod and the locking nut. When the injector is activated the drive nut is rotated and since the plunger rod is prevented from rotational movement by the locking nut the result is an axial movement of the plunger rod towards the plunger of the medicament container such that an amount of medicament is expelled through an injection needle of the delivery device.

SUMMARY OF THE INVENTION

It is an object of the invention to provide a medicament delivery device with improved reliability in operation. This object and other objects are solved by a medicament delivery device as defined in claim 1. Preferred embodiments of the present invention are defined in the dependent claims.

Thus, in accordance with an aspect of the present invention, there is provided a medicament delivery device which comprises a rear housing and a container housing that are releasably connected to each other and a medicament container comprising a plunger can be received and held within the container housing. The rear housing comprises a plunger rod which is arranged to act on the plunger of said medicament container when the medicament container is placed in said container housing. Further, a drive mechanism is arranged in the rear housing to drive the plunger rod and a locking mechanism is arranged for locking the plunger rod. The locking mechanism comprises a locking wheel and locking means which are moveable between an active position where the locking means prevent the locking wheel from rotation and an inactive position where the locking means allow the locking wheel to rotate. The plunger rod extends through an opening in the locking wheel and the plunger rod and the opening in the locking wheel are arranged to mate with each other such that axial movement of the plunger rod relative to the locking wheel is allowed while rotation of said plunger rod relative to the locking wheel is prevented. A resilient member is arranged to act on the moveable locking means to bias the movable looking means towards the inactive position where the locking means allow the locking wheel to rotate.

In the prior art solution described in WO-2009/101005 the moveable locking member is biased towards the inactive position by means of the elastic properties of the locking member itself. In course of time, these biasing elastic properties diminish and the moveable locking means may remain in their locking position even at times when they should assume their inactive position. Due to the fact that the present invention provides a separate resilient member to bias the movable locking means towards the inactive position, the risk that fatigue of the material of the locking member causes the locking member to remain in the active position is greatly reduced thus enhancing the useful service life of the delivery device as well as improving user friendliness.

In accordance with an embodiment of the medicament delivery device, the moveable locking means comprises at least one flexible arm having a cogged segment which in the active position engages with a cogged surface of the locking wheel. The cogged surfaces of the locking means and the locking wheel provide for reliable locking of the plunger rod when the locking means are in the active position.

In accordance with an embodiment of the medicament delivery device, the moveable locking means comprise two flexible arms, each having a cogged segment which in the active position engages with a cogged surface of the locking wheel. The provision of two locking means further enhances the reliability of the locking action and tilting and off-centre positioning of the locking wheel can be avoided.

In accordance with an embodiment of the medicament delivery device, the locking mechanism comprises a hollow casing arranged at the rear housing and wherein the flexible arms are formed in recesses provided in an outer wall of the casing, the locking wheel is arranged within said hollow casing such that the cogged surfaces of the flexible arms and the locking wheel interact when said moveable locking means are in their active position. This construction ensures reliable functioning of the locking mechanism. The locking wheel can rotate freely within the casing as long as the locking means are in their inactive position and as soon as they assume their active position, the locking wheel is securely locked.

In accordance with an embodiment of the medicament delivery device, the container housing, when connected to the rear housing, engages with the moveable locking means and forces said moveable locking means into their active position. This assures that as soon as the container housing is mounted to the rear housing, which is the case when a user has replaced an empty container with a new one, the locking means are automatically forced into their active position and no further action is required from the user in order to obtain a delivery device ready for use.

In accordance with an embodiment of the medicament delivery device, the container housing is releasably mounted in a locking ring which in turn can be releasably connected to said rear housing, wherein said locking ring, when connected to the rear housing, engages with the moveable locking means and forces said moveable locking means into their active position. Often, the container is delivered in a container housing from the medicament supplier. When a user needs to replace an empty or otherwise finished container, the container housing with the container inside is slipped into the locking ring and the locking ring is then attached to the rear housing. As this is done, the locking ring will automatically cause the locking means to assume their active position.

In accordance with an embodiment of the medicament delivery device, the moveable locking means comprises protrusions extending outwardly. The protrusion provides for a reliable interaction with e.g. container housing or locking ring.

In accordance with an embodiment of the medicament delivery device, the resilient member comprises a wire spring. A wire spring is a cheap, reliable and predictable spring element that can easily be mounted within the delivery device.

In accordance with an embodiment of the medicament delivery device, the wire spring has two opposed ends, each arranged at a separate flexible arm. The ends of the wire spring can be adhered to the flexible arms by means of adhesive, fusing or by mechanical means.

In accordance with an embodiment of the medicament delivery device, the hollow casing has a cylindrical cross-section and the moveable locking means are arranged diametrically opposite each other and wherein the wire spring is arranged to follow the contour of the outer wall of the hollow casing. This provides for a balanced and space-effective construction of the locking mechanism.

In accordance with an embodiment of the medicament delivery device, the resilient member comprises a sheet metal spring. A sheet metal spring is very space saving and can be provided with high spring rates to achieve reliable functioning of the locking mechanism.

In accordance with an embodiment of the medicament delivery device, the resilient member comprises a sheet metal spring which is mounted along an inner surface of the outer wall of the casing. This is a very space effective manner of constructing the locking mechanism.

In accordance with an embodiment of the medicament delivery device, the flexible arms extend in a direction perpendicular to the longitudinal direction of the plunger rod. This is advantageous if it is necessary to reduce the length of the locking mechanism.

In accordance with an embodiment of the medicament delivery device, the flexible arms extend in a direction parallel to the longitudinal direction of the plunger rod. This is advantageous if it is desirable to reduce the thickness of the delivery device.

DESCRIPTION OF PREFERRED EMBODIMENTS

Embodiments of the present invention will now be described in detail. As should be noted in the present application, when the term "distal or rear part/end" is used, this refers to the part/end of the delivery device, or the parts/ends of the members thereof, which is/are located the furthest away from the medicament delivery site of the patient. Correspondingly, when the term "proximal or front part/end" is used, this refers to the part/end of the delivery device, or the parts/ends of the members thereof, which, is/are located closest to the medicament delivery site of the patient.

Below, two embodiments of the present invention are described. Common for these embodiments is that the medicament delivery device comprises a dose setting mechanism for setting and resetting a dose of medicament to be delivered, a drive device comprising a drive nut which is rotatably connected to the plunger rod, an energy accumulating member such as a spirally wound leaf spring arranged to receive, store and release energy necessary for delivery of a dose and an activating member for activating the medicament delivery device when a dose is set and a user is ready to inject the medicament. The drive nut is preferably provided with an opening having an internal thread arranged to interact with an outer thread provided on the plunger.

Figure 1:
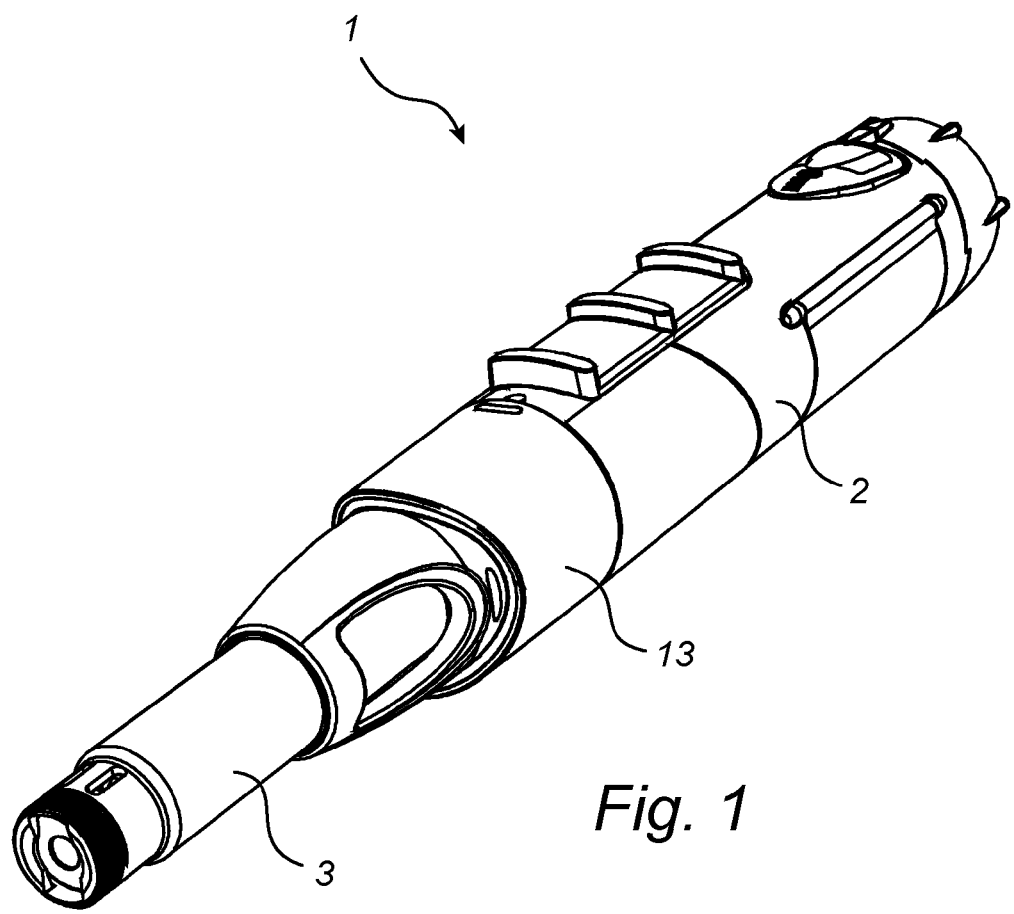
FIG. 1 shows a perspective view of an embodiment of the delivery device in accordance with the present invention.

In an embodiment of a medicament delivery device of the invention, as shown in FIG. 1, the medicament delivery device 1 comprises a rear housing 2, a container housing 3 and a locking ring 13 by means of which the rear housing 2 and the container housing 3 is releasably connected to each other.

Figure 2:
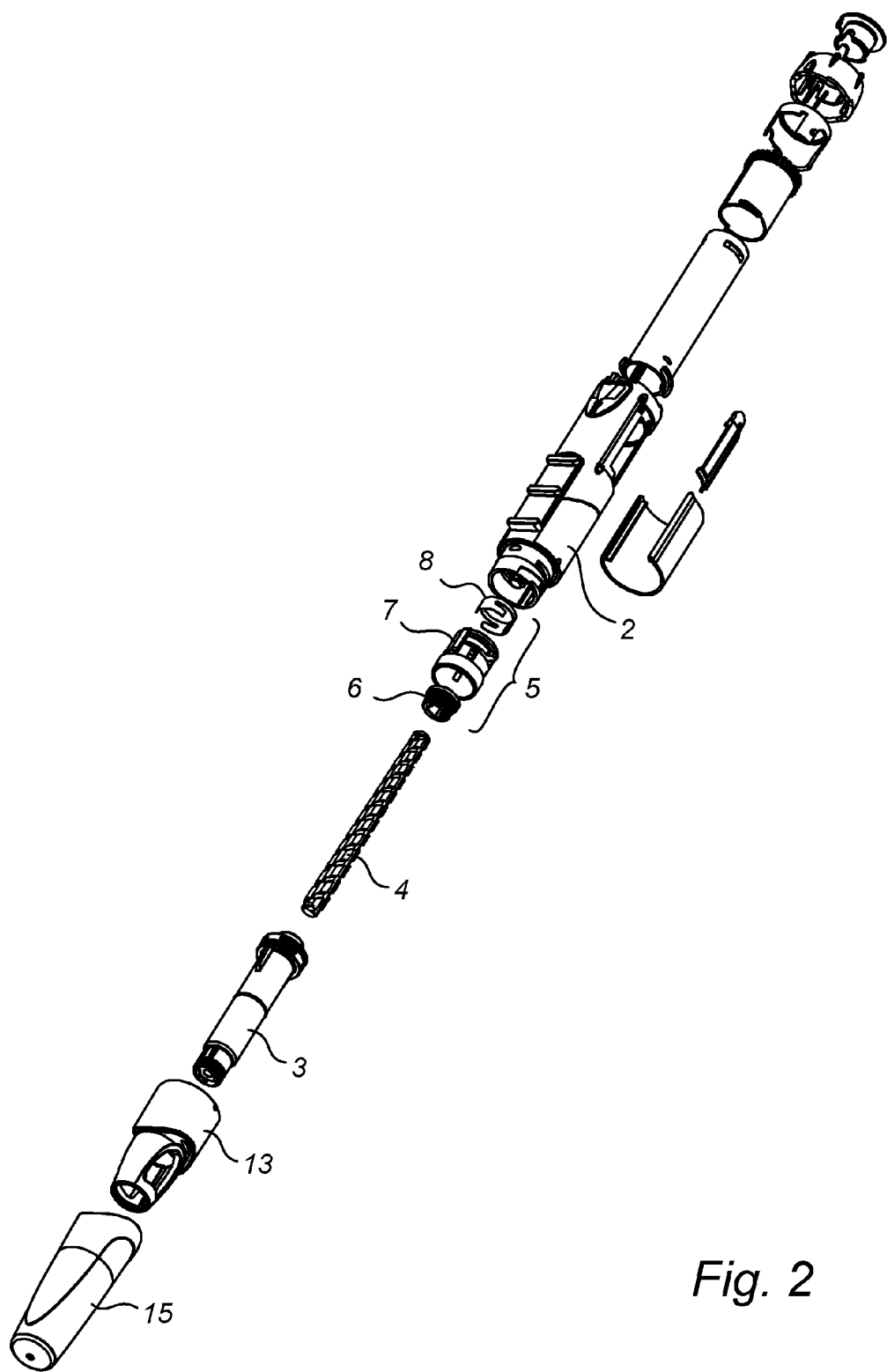
FIG. 2 shows an exploded view of a first embodiment of the delivery device in accordance with the present invention.
Figure 3:
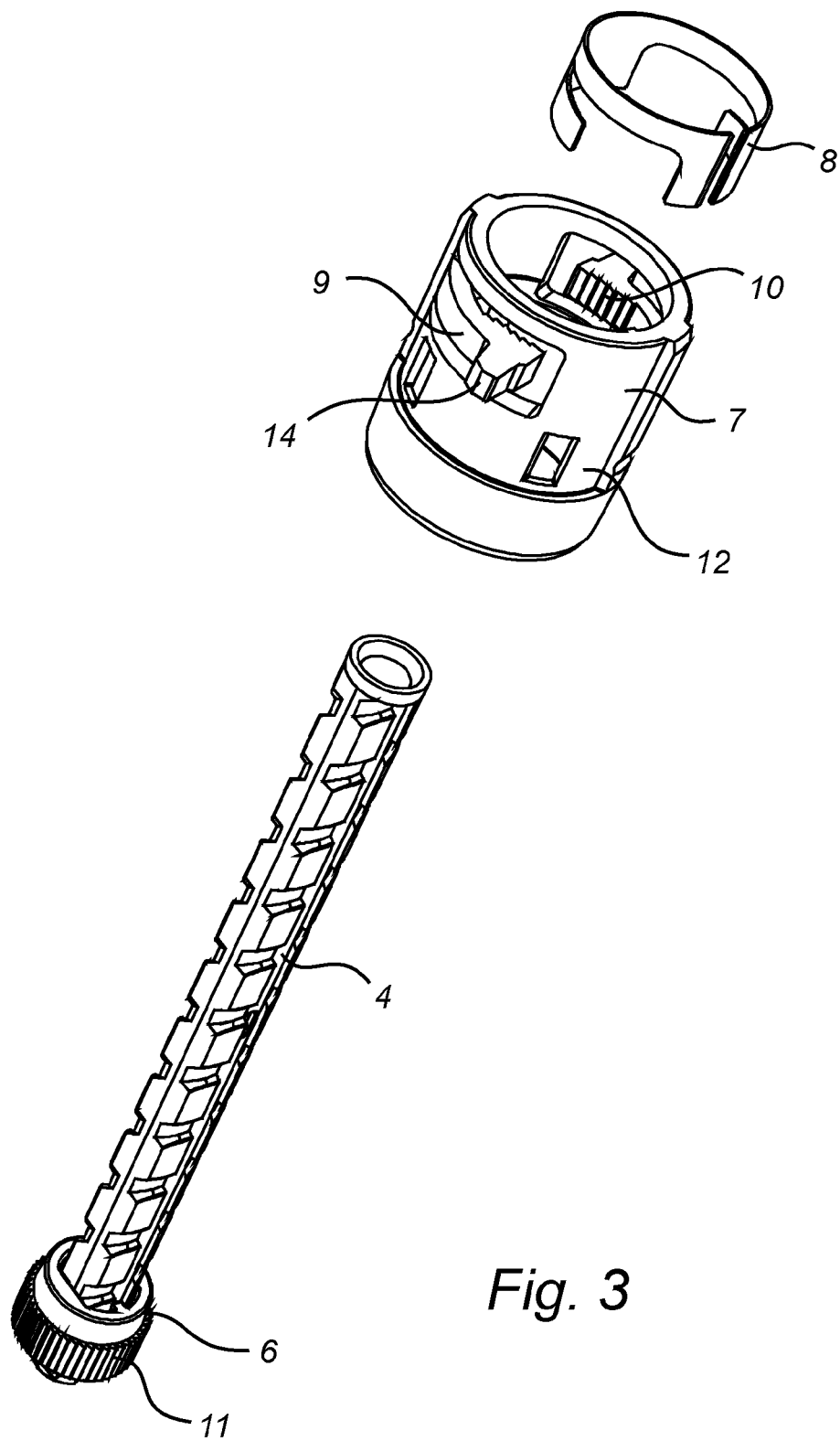
FIG. 3 shows an exploded view of the locking mechanism of a first embodiment of the delivery device in accordance with the present invention.
Figure 4:
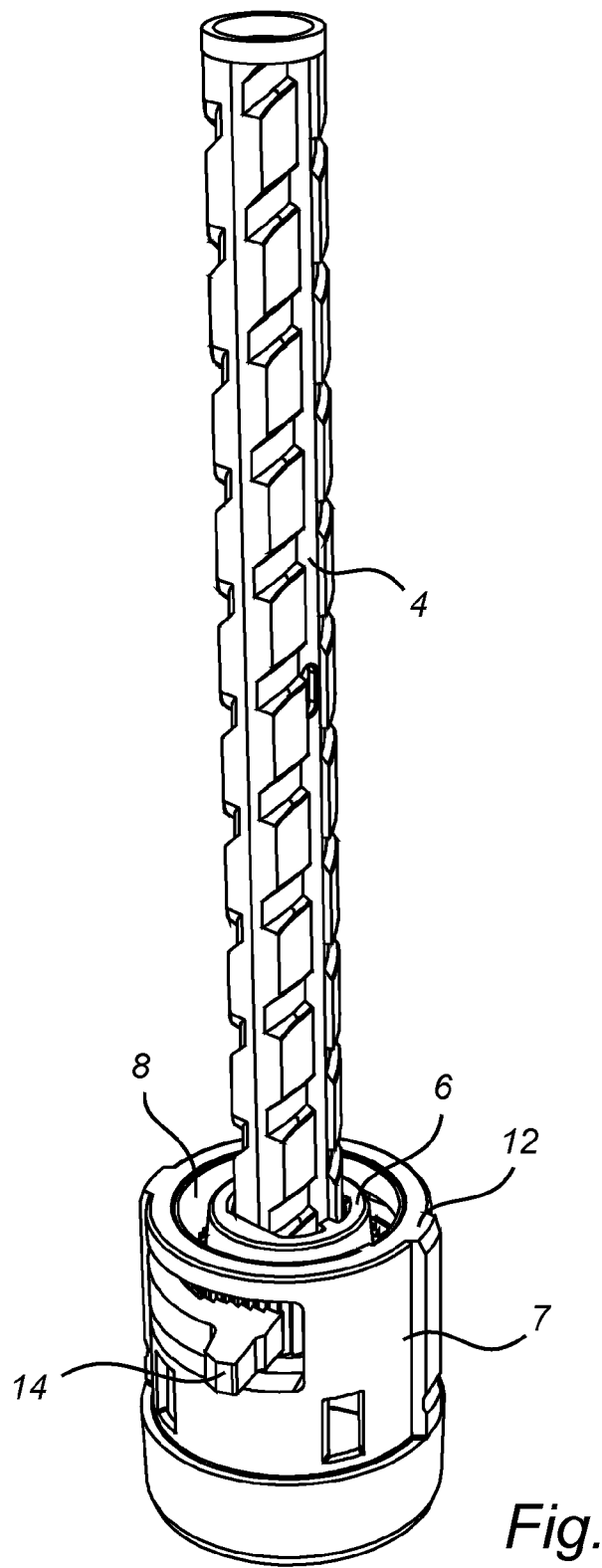
FIG. 4 shows a perspective view of the locking mechanism of a first embodiment of the delivery device in accordance with the present invention.
Figure 5A:
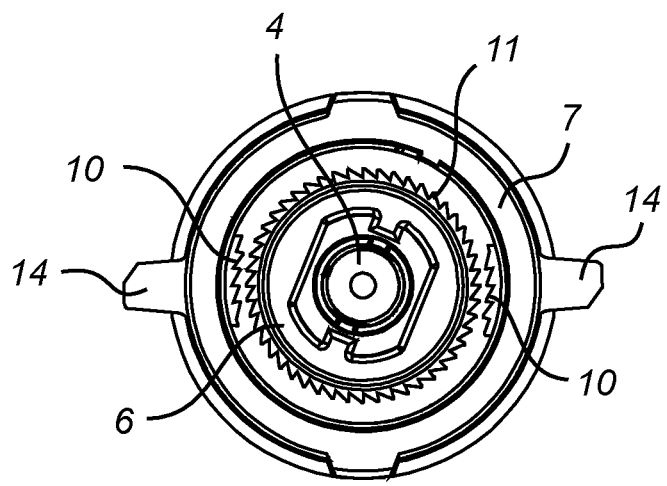
FIGS. 5a and 5b show top views of the locking mechanism of a first embodiment of the delivery device in accordance with the present invention.
Figure 5B:
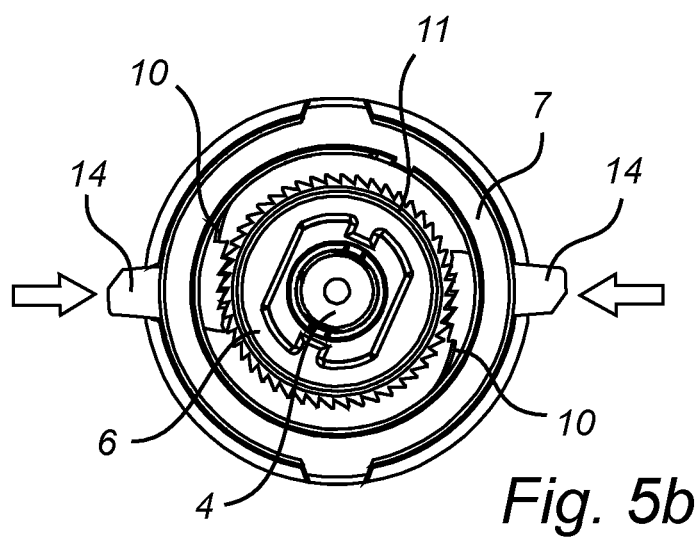

FIG. 2 shows an exploded view of a first embodiment of the medicament delivery device in accordance with the present invention. This figure shows the structure of the device and in particular the interaction between the plunger rod 4 and the locking mechanism 5. Within rear housing 2 but not shown in the figure is a drive mechanism with a drive nut which is rotatably connected to the plunger rod 4 by means of an inner thread of an opening in the drive nut and an outer thread provided on said plunger rod 4. Container housing 3 holds a medicament container such as a syringe or a cartridge having a delivery member such as a needle. The delivery member may also be adapted to be mounted on a front end of the container housing 3 by any conventional means such as a threaded coupling or a bayonet coupling. The delivery member may be a needle, a nozzle or a mouthpiece. The container further comprises a moveable plunger with which the plunger rod interacts when medicament is expelled from the container. The container housing 3 is connected to the rear housing 2 preferably by means of locking ring 13 which in the mounted state forms a part of the outer hull of the medicament delivery device. A locking mechanism 5 is arranged between the container housing 3 and the drive mechanism which is located within the rear housing 2. The locking mechanism 5 will be described in greater detail below. A cap 15 is arrangeable to cover the container housing when the medicament delivery device is not in use in order to avoid accidental needle stick injuries, if the delivery member is a needle, and to protect the delivery member from damage.

Referring to now FIGS. 3, 4, 5a and 5b a locking mechanism 5 according to a first embodiment of the present invention will be described. The locking mechanism 5 comprises a resilient member 8, a locking means 7 and a locking wheel 6 provided with a cogged surface 11. The locking means 7, in turn, comprise a hollow casing 12 and two flexible locking arms 9. Each flexible locking arm 9 comprises a cogged surface 10 which, when the locking arms are in their active position, engages with the cogged surface 11 of the locking wheel 6. The locking wheel 6 comprises an opening through which the plunger rod 4 extends and they have corresponding shapes such that any relative rotational movement between the plunger rod 4 and the locking wheel 6 is prevented while axial relative movement is allowed. This means that when the flexible arms 9 are in their inactive position, the plunger rod is allowed to rotate as well as to move axially, see FIG. 5a. On the other hand, when the flexible arms 9 are in their active position, i.e. the cogged segments 10 interacting with the cogged surface 11, the plunger rod can move axially but any rotational movement is prevented, see FIG. 5b. Positioned adjacent to the inner surface of the outer wall of the hollow casing 12 is a resilient member 8 in the form of a sheet metal spring. The sheet metal spring is arranged to bias the flexible arms 9 towards their inactive position.

Referring to FIGS. 1-4, 5a and 5b the functioning of the delivery device according to a first embodiment of the present invention is described. When a container held within container housing 3 is emptied, or otherwise in a state that requires replacement, locking ring 13 is removed from the rear housing 2. The locking ring 13 may be connected to the rear housing 2 by means of a thread or any other suitable connection. When this is done the container housing 3 is removed and usually replaced with a new container housing comprising a container therein. It is of course also possible to reuse the container housing 3 and only replace the container itself. A new, or the reused, container housing 3 is arranged to extend through the locking ring 13 and is maneuvered towards the rear housing 2. Since, in most cases, the old cartridge was empty the plunger rod 4 will now be in its most extended position and will have to be re-positioned to its retracted position. Due to the fact that the plunger rod 4 is rotatably connected to the drive mechanism, this axial re-positioning is only possible if the plunger rod 4 is allowed to rotate. As long as the flexible arms 9 are in their active position, rotation of the plunger rod 4 is prevented. However, since the locking ring 13 is not coupled to the rear housing at this stage, the flexible arms 9 are forced by the resilient member 8, in this case a sheet metal spring, to their inactive position and therefore plunger rod 4 is allowed to rotate. The user forces the plunger rod 4 back to its retracted position by placing the plunger of the container against the plunger rod 4 and simply force the plunger rod 4 backwards. Advantageously, a resilient member is provided acting on the plunger rod 4 and a distal part of the rear housing forcing the plunger rod towards its extended position thereby ensuring that the end of the plunger rod 4 remains in contact with the plunger of the container at all time. When the container has fully re-positioned the plunger rod 4 the locking ring 13 is again coupled to the rear housing 2 by for example a threaded connection, snap fit connection or any other suitable connection. During the coupling of the locking ring 13 to the rear housing 2, the protrusions 14 on flexible arms 9 contacts an inner surface of locking ring 13 and the flexible arms 9 are forced to assume their active position again, against the bias of the resilient member 8. Since any rotation of the plunger rod 4 is prevented at this stage, any rotational movement of the drive nut will cause the plunger rod to perform an axial motion. And, since the plunger rod 4 at all times will be in contact with the plunger of the container, the medicament delivery device is immediately ready to expel a preferred dosis of a medicament. Preferably, the proximal end of the plunger rod 4, i.e. the end facing a plunger of a container, is provided with a spinner to reduce friction against the plunger.

Figure 6:
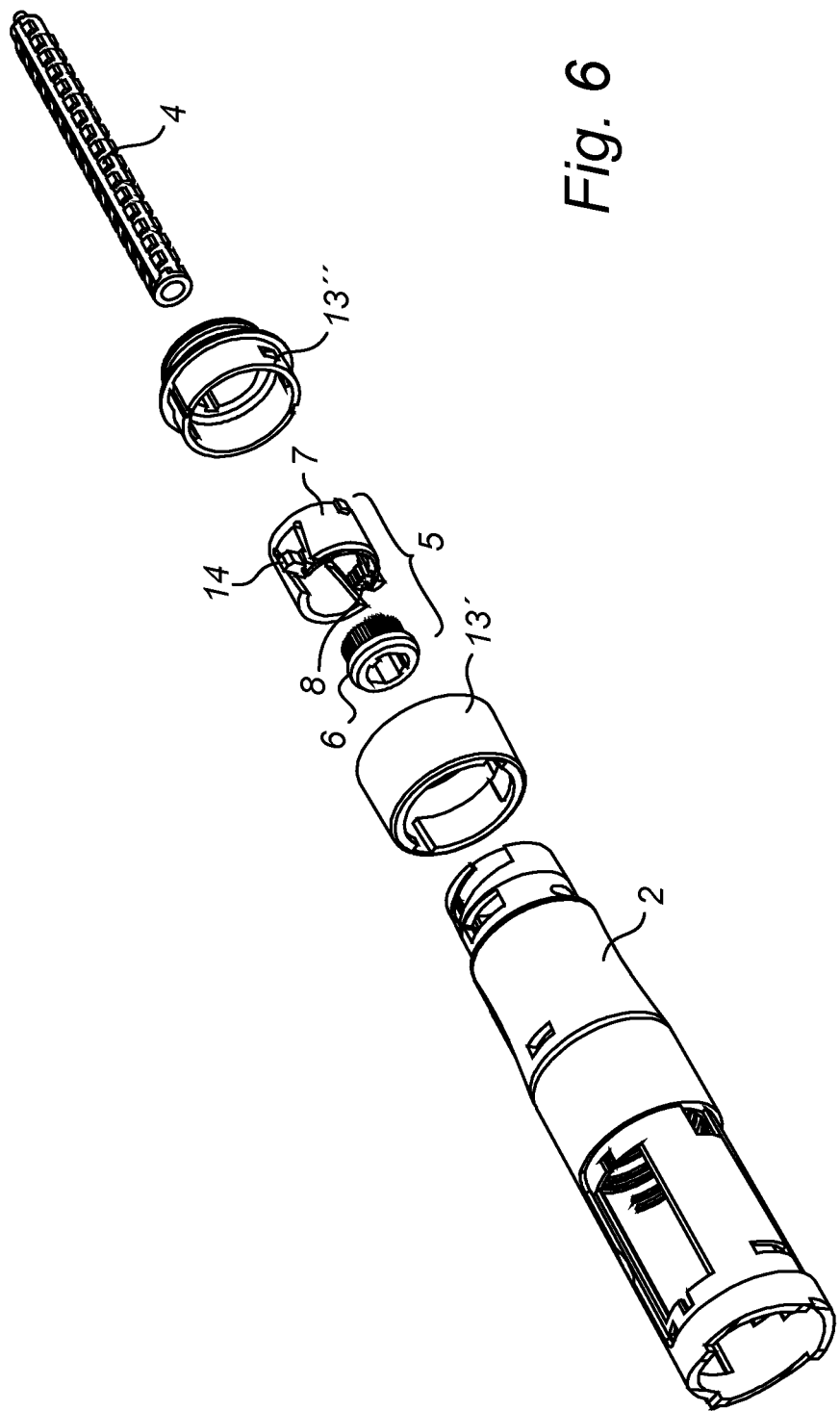
FIG. 6 shows an exploded view of the locking mechanism of a second embodiment of the delivery device in accordance with the present invention.
Figure 7:
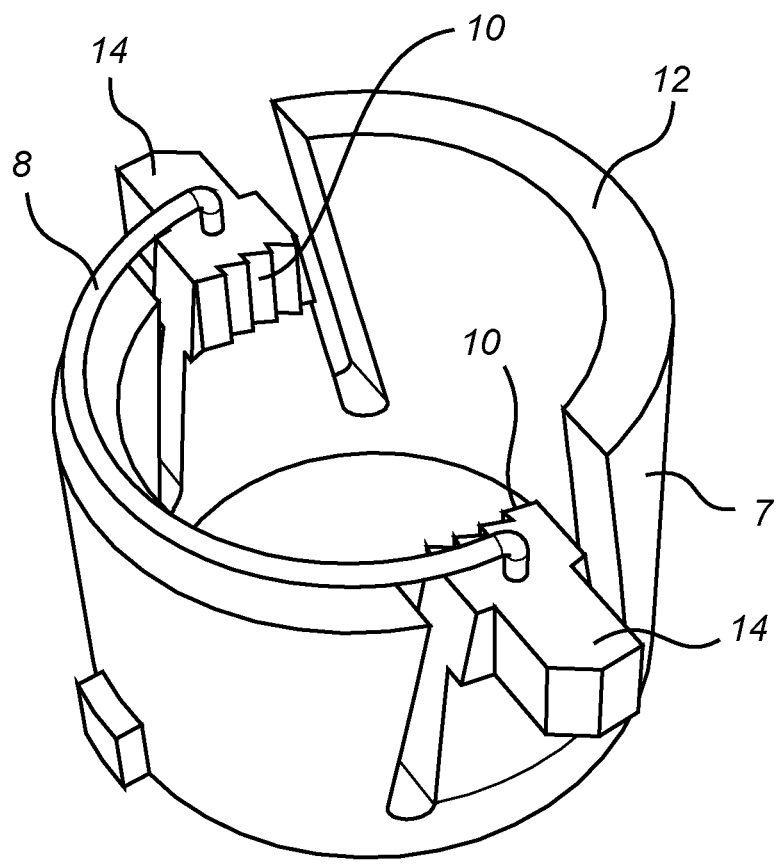
FIG. 7 shows a perspective view of a part of the locking mechanism of a second embodiment of the delivery device in accordance with the present invention.

Referring to FIGS. 6 and 7, a second embodiment of the medicament delivery device according to the present invention is described. In this embodiment the resilient member 8 is constituted by a wire spring instead of a sheet metal spring. The wire spring is attached with one end to each of two flexible arms 9 extending in a direction generally parallel to the longitudinal axis of the plunger rod 4. Similar to the flexible arms 9 described earlier, these are provided with cogged segments 10 intended to interact with a cogged surface 11 provided on locking wheel 6. Locking ring 13 comprises two parts 13' and 13" shown in FIG. 6 as separate details. In use, however, they are normally considered as a single detail, namely locking ring 13. Similar to the first embodiment shown in previous figures, locking mechanism 5 is arranged within rear housing 2. When a container has been emptied, the container housing, not shown in FIG. 6, is disassembled together with locking ring 13. As this is done, the wire spring 8 springs out, forcing the flexible arms 9 to assume their inactive position. A container housing comprising a new container is mounted to the rear housing 2 and as soon as the locking ring 13 is brought into position on the rear housing, the flexible arms 9 are again forced to their active position and the medicament delivery device is ready to be used.

Finally, it is understood that a medicament delivery device according to the present invention has a number of advantages over the prior art devices. The flexible arms of known devices are prone to fatigue which results in devices where the plunger rod can no longer be retracted, or hardly retracted, since the flexible arms do not assume their inactive position even though they are no longer forced into their active position. These flexible arms are generally made from plastic and the resilient properties of that material deteriorate with time such that the arms will be permanently deformed and do not spring back to their inactive position. If the plunger rod is forced back, even though the cogged segments of the flexible arms are still in contact, fully or partly, with the cogged surface of the locking wheel, the cogged segments and the cogged surface will wear out quickly. In a worst case scenario, this could affect the functioning of the medicament delivery device since a reliable locking of the plunger rod against rotation no longer can be guaranteed. Furthermore, retracting of the plunger rod with the flexible arms and the locking wheel in engagement causes a non-negligible noise.

It is to be understood that the embodiments described above and in the drawings are to be regarded only as non-limiting examples of the invention and that they may be modified in many ways within the scope of the claims.

The invention claimed is:

1. A medicament delivery device, comprising:
    a container housing arranged to receive and hold a medicament container having a plunger; and
    a rear housing releasably connected to the container housing and comprising:
        a plunger rod arranged to act on the plunger when the medicament container is received in the container housing;
        a drive mechanism arranged to drive the plunger rod; and
        a locking mechanism for locking the plunger rod, comprising:
            a locking wheel;
            a locking device movable between an active position, in which the locking device prevents rotation of the locking wheel, and an inactive position, in which the locking device allows rotation of the locking wheel, wherein the plunger rod extends through an opening in the locking wheel, and the plunger rod and the opening in the locking wheel are arranged to mate with each other such that axial movement of the plunger rod relative to the locking wheel is allowed while rotation of the plunger rod relative to the locking wheel is prevented; and
a resilient member arranged at the movable locking device and to act on the movable locking device to displace the movable locking device toward the inactive position;
wherein the locking device comprises at least one flexible arm having a cogged segment which in the active position engages with a cogged surface of the locking wheel.

2. The medicament delivery device of claim 1, wherein the locking mechanism further comprises a hollow casing arranged at the rear housing, and the at least one flexible arm is formed in at least one recess provided in an outer wall of the casing, the locking wheel is arranged within the hollow casing such that the cogged segment of the at least one flexible arm and the locking wheel interact when the locking device is in the active position.

3. The medicament delivery device of claim 1, wherein the container housing, when connected to the rear housing, engages with the locking device and forces the locking device into the active position.

4. The medicament delivery device of claim 1, wherein the container housing is releasably mounted in a locking ring releasably connected to the rear housing; and the locking ring, when connected to the rear housing, engages with the locking device and forces the locking device into the active position.

5. The medicament delivery device of claim 1, wherein the locking device comprises protrusions extending outwardly.

6. The medicament delivery device of claim 2, wherein the resilient member comprises a sheet metal spring mounted along an inner surface of the casing.

7. The medicament delivery device of claim 1, wherein the flexible arms extend in a direction perpendicular to a longitudinal direction of the plunger rod.

8. The medicament delivery device of claim 1, wherein the flexible arms extend in a direction parallel to a longitudinal direction of the plunger rod.

9. The medicament delivery device of claim 1, wherein the medicament delivery device is a reusable injector.

10. The medicament delivery device of claim 1, wherein the medicament delivery device is a reusable inhaler.

11. A medicament delivery device, comprising:
a container housing arranged to receive and hold a medicament container having a plunger; and
a rear housing releasably connected to the container housing and comprising:
a plunger rod arranged to act on the plunger when the medicament container is received in the container housing;
a drive mechanism arranged to drive the plunger rod; and
a locking mechanism for locking the plunger rod, comprising:
a locking wheel;
a locking device movable between an active position, in which the locking device prevents rotation of the locking wheel, and an inactive position, in which the locking device allows rotation of the locking wheel, wherein the plunger rod extends through an opening in the locking wheel, and the plunger rod and the opening in the locking wheel are arranged to mate with each other such that axial movement of the plunger rod relative to the locking wheel is allowed while rotation of the plunger rod relative to the locking wheel is prevented; and
a resilient member arranged at the movable locking device and to act on the movable locking device to displace the movable locking device toward the inactive position, wherein the resilient member comprises a wire spring.

12. The medicament delivery device of claim 11, wherein the locking device comprises two flexible arms, each having a cogged segment which in the active position engages with a cogged surface of the locking wheel; and the wire spring has two opposed ends, each arranged at a different flexible arm.

13. The medicament delivery device of claim 12, wherein the locking mechanism further comprises a hollow casing arranged at the rear housing; the flexible arms are formed in recesses provided in an outer wall of the casing; the locking wheel is arranged within the hollow casing such that cogged segments of the flexible arms and the locking wheel interact when the locking device is in the active position; the hollow casing has a cylindrical cross-section; the flexible arms are arranged diametrically opposite each other; and the wire spring is arranged to follow a contour of an outer wall of the hollow casing.

14. A medicament delivery device, comprising:
a container housing arranged to receive and hold a medicament container having a plunger; and
a rear housing releasably connected to the container housing and comprising:
a plunger rod arranged to act on the plunger when the medicament container is received in the container housing;
a drive mechanism arranged to drive the plunger rod; and
a locking mechanism for locking the plunger rod, comprising:
a locking wheel;
a locking device movable between an active position, in which the locking device prevents rotation of the locking wheel, and an inactive position, in which the locking device allows rotation of the locking wheel, wherein the plunger rod extends through an opening in the locking wheel, and the plunger rod and the opening in the locking wheel are arranged to mate with each other such that axial movement of the plunger rod relative to the locking wheel is allowed while rotation of the plunger rod relative to the locking wheel is prevented; and
a resilient member arranged at the movable locking device and to act on the movable locking device to displace the movable locking device toward the inactive position, wherein the resilient member comprises a sheet metal spring.

* * * * *